United States Patent
Chung et al.

(10) Patent No.: US 9,096,828 B2
(45) Date of Patent: Aug. 4, 2015

(54) METHOD AND DEVICE FOR SEPARATING CHARGED PARTICLES IN LIQUID SAMPLE AND MANUFACTURING METHOD OF THE DEVICE

(71) Applicant: NATIONAL CHENG KUNG UNIVERSITY, Tainan (TW)

(72) Inventors: Chen-Kuei Chung, Tainan (TW); Hsien-Chang Chang, Tainan (TW); Chia-Chern Chen, Tainan (TW); Cheng-Ting Li, Kaohsiung (TW); Chia-Cheng Tu, Zhongli (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 103 days.

(21) Appl. No.: 13/837,182

(22) Filed: Mar. 15, 2013

(65) Prior Publication Data

US 2013/0252228 A1    Sep. 26, 2013

(30) Foreign Application Priority Data

Mar. 23, 2012 (TW) .............................. 101110240 A

(51) Int. Cl.
| | |
|---|---|
| *G01N 27/453* | (2006.01) |
| *C12N 5/078* | (2010.01) |
| *B03C 5/00* | (2006.01) |
| *C12M 1/00* | (2006.01) |
| *B03C 5/02* | (2006.01) |

(52) U.S. Cl.
CPC .............. *C12N 5/0634* (2013.01); *B03C 5/005* (2013.01); *C12M 47/04* (2013.01); *B03C 5/022* (2013.01); *Y10T 29/49155* (2015.01)

(58) Field of Classification Search
CPC ................................. B03C 5/005; B03C 5/022
USPC ..................... 204/547, 643, 450, 600; 422/73
See application file for complete search history.

(56) References Cited

U.S. PATENT DOCUMENTS

| | | | | |
|---|---|---|---|---|
| 5,993,630 | A  * | 11/1999 | Becker et al. ................. | 204/547 |
| 6,352,838 | B1 * | 3/2002  | Krulevitch et al. ............ | 435/34 |
| 2002/0182654 | A1 * | 12/2002 | Jing et al. .................... | 435/7.21 |

FOREIGN PATENT DOCUMENTS

| | | |
|---|---|---|
| TW | 201124709 A1 | 7/2011 |
| TW | 201331582 A1 | 8/2013 |

* cited by examiner

*Primary Examiner* — Alex Noguerola
(74) *Attorney, Agent, or Firm* — Muncy, Geissler, Olds & Lowe, P.C.

(57) ABSTRACT

A method for separating charged particles in a liquid sample is disclosed. The method includes the steps of driving the liquid sample containing a plurality of charged particles to flow, forming a non-uniform electric field in the direction relative to the flow direction of the liquid sample by two electrodes, and aggregating the charged particles under the non-uniform electric field so as to separating the charged particles from the liquid sample. When the liquid sample flows through the non-uniform electric field, it doesn't contact to the electrodes. A device and its manufacturing method for separating charged particles in a liquid sample are also disclosed. Accordingly, the charged particles can be separated from the liquid sample easily and more effectively.

17 Claims, 6 Drawing Sheets

METHOD AND DEVICE FOR SEPARATING CHARGED PARTICLES IN LIQUID SAMPLE AND MANUFACTURING METHOD OF THE DEVICE

CROSS REFERENCE TO RELATED APPLICATIONS

This Non-provisional application claims priority under 35 U.S.C. §119(a) on Patent Application No(s). 101110240 filed in Taiwan, Republic of China on Mar. 23, 2012, the entire contents of which are hereby incorporated by reference.

BACKGROUND OF THE INVENTION

1. Field of Invention

The present invention relates to a separating method and device, and in particular, to a method and device for separating charged particles in a liquid sample.

2. Related Art

Blood plasma is an important biological specimen capable of providing physiological or clinical information for medical or inspection unit to quickly comprehend the condition of a subject. Otherwise, blood plasma is also advantageous for showing the physiological condition of specific time point.

To achieve the above-mentioned purpose, many kinds of blood tests have to be well conducted with the blood plasma separated from whole blood. For example, blood coagulation test and cell-mediated or non cell-mediated immune response test of blood. All these tests are based on excellent blood plasma separation. Hence, multiple researches and developments are conducted regarding to the above needs in purpose of providing a method with excellent and fast separation to separate blood plasma from whole blood.

However, the conventional blood plasma separation needs to be conducted in the laboratory with centrifugation method. The centrifugation method is to store the whole blood into a test tube with anticoagulant; then, to centrifuge with high speed to separate different substances with different specific density, further to separate the blood cell and the blood plasma. But, the centrifuge is bulky, and the pre-treatment of sample, the standby procedure and the cleanness of the centrifuge are time-consuming. In addition, the transportation of the sample from hospital to laboratory is also time-consuming, which is inconvenient for medical personnel who need to know the test result at very short time. The centrifuge in the hospital or laboratory utilize large amount of blood samples in one time; however, most tests only need a small amount of blood plasma sample to get the desired result. Excess samples may cause the problems of recycling or pollution. Moreover, professional stuffs for operating the centrifuge are needed to be trained in advance, thus raising the cost.

In recent years, the techniques of biomedical inspection apparatus advance significantly, especially in the aspect of chips design. These newly developed tools are in replace of the conventional inspection devices with bulky volume, providing better applicability and operability. Lately, the micro fluidic chips used to separate blood plasma includes electrophoresis technique, dielectrophoresis technique, filter or changing the geometry of the flow channel.

Although it is easier to operate the electrophoresis or dielectrophoresis techniques, the electrophoresis or dielectrophoresis techniques need to be done under high voltage. Otherwise, it is not easy to manufacture the microchannel and install the filter. The method of changing the geometry of microchannel has to apply a micro pump to drive the sample, which easily caused qualitative change of the sample. Furthermore, using the external force to drive the sample to flow in the channel, including the early artificial pressing syringe and the recent pump, may limit the miniaturization of the chip, further increasing the manufacturing cost and complexity.

Therefore, it is an important subject to provide an apparatus for separating the blood plasma from Whole blood efficiently without external force, further making the blood plasma separation process more instant and simpler.

SUMMARY OF THE INVENTION

In view of the foregoing, it is an objective of the present invention to provide an apparatus for separating the blood plasma from whole blood efficiently without external force, further making the blood plasma separation process to obtain instantaneity and simplicity.

To achieve the above objective, the present invention discloses a method for separating charged particles in a liquid sample, comprising the steps of: driving the liquid sample containing a plurality of the charged particles to flow; forming a non-uniform electric field in a direction relative to the flow direction of the liquid sample by two electrodes; and aggregating the charged particles under the non-uniform electric field so as to separating the charged particles from the liquid sample. When flowing through the non-uniform electric field, the liquid sample doesn't contact to the electrodes. Preferably, the liquid sample is a blood sample, and the charged particles are blood cells.

In one embodiment, the liquid sample flows within a channel and is driven by a capillary attraction of the channel to flow.

In one embodiment, the non-uniform electric field is formed by the two electrodes, and the sides of the electrodes opposite to each other have different surface areas.

In one embodiment, the liquid sample flows within a channel and the channel is disposed between the two electrodes.

In one embodiment, the mass density of the charged particles is larger than the density of the liquid sample, and the charged particles are separated from the liquid sample by the non-uniform electric field and gravity.

To achieve the above objective, the present invention also discloses a device for separating charged particles in a liquid sample. The device includes a substrate layer, an interlaid layer, a cover layer, and two electrodes. The interlaid layer is disposed on the substrate layer, and the cover layer is disposed on the interlaid layer. The substrate layer, the interlaid layer and the cover layer together define a channel. The two electrodes are correspondingly disposed on the cover layer and the substrate layer, respectively. Herein the electrodes do not contact with the liquid sample. The device is a capacitive or resistive separation chip, the liquid sample is a blood sample, and the charged particles are blood cells.

In one embodiment, the material of the substrate layer and/or the cover layer comprises glass, ITO, silicon oxide, or silicon.

In one embodiment, the material of the interlaid layer comprises an optical paste or a photoresist material.

In one embodiment, the cover layer has an opening and an outlet communicating with the channel, and one end of the channel close to the opening has a larger internal diameter.

In one embodiment, the channel has at least a tuning portion with a shape of arc, hairpin, or hoof.

In one embodiment, one of the electrodes is disposed over the cover layer, and the other one thereof is disposed underneath the substrate layer.

In one embodiment, the sides of the electrodes opposite to each other have different surface areas so as to form a non-uniform electric field.

In one embodiment, one of the electrodes has a shape and a dimension identical to the channel, and the other one thereof has a shape and a dimension identical to the substrate layer.

To achieve the above objective, the present invention further discloses a manufacturing method of the above-mentioned device, which includes the steps of: forming an opening and an outlet on the cover layer; forming two electrodes on the cover layer and the substrate layer, respectively; disposing an optical paste or a photoresist material on the substrate layer to form the interlaid layer; processing the interlaid layer; and combining the cover layer, the interlaid layer and the substrate layer to together define a channel. Herein, the channel does not contact with the electrodes.

In one embodiment, the step of forming the electrodes comprises to dispose a thermal resist material or another photoresist material on the cover layer and the substrate layer for defining the patterns of the electrodes and to coat a layer of electrode material thereon. Herein, the patterns are defined by a laser machining or a photolithography process.

In one embodiment, the step of processing the interlaid layer is to form a part of the channel by a laser machining, a photolithography process, or a mechanical machining.

In one embodiment, the cover layer, the interlaid layer and the substrate layer are combined by a low-temperature bonding process.

As mentioned above, the method for separating charged particles in liquid sample is applied by making the liquid sample pass through a non-uniform electric field. The direction of the non-uniform electric field is relative to the flow direction of the sample; preferably, the direction of the non-uniform electric field is vertical to the flow direction of the sample. With the non-uniform electric field, the charged particles of the liquid sample are able to aggregate, further be separated from the liquid sample. With the above-mentioned techniques, users can collect separated charged particles or the liquid sample being separated.

With regard to the separating device, a substrate layer, an interlaid layer, a cover layer and two electrodes of the separating device defines a channel which is used for accommodating the liquid sample. The non-uniform electric field formed by the corresponding disposition of the two electrodes is applied to the liquid sample flowing through, further aggregating the charged particles and slowing down the flow rate. As mentioned above, the separating device of the present invention has simple structure. With some simple operating steps including insertion of the liquid sample and formation of the electric field, the separating device is advantageous for simple operation and quick separation.

Compared to the prior techniques, the method and device for separating charged particles in liquid sample and manufacturing method of the device of the present invention is suitable for separating whole blood and collecting blood plasma. The separation is done by aggregating the charged blood cells with non-uniform electric field, thus making the difference flow rate between the blood cells and blood plasma. The materials of the substrate layer and the upper layer are both hydrophilic, which driving the sample to be tested without external force and the need of pump, reducing the bulk and the manufacturing cost. In addition, the separating device is advantageous for its disposability, lower possibilities of the qualitative change and pollution of the sample. Moreover, the device is able to be applied without cleanness and special preprocessing.

BRIEF DESCRIPTION OF THE DRAWINGS

The invention will become more fully understood from the detailed description and accompanying drawings, which are given for illustration only, and thus are not limitative of the present invention, and wherein:

FIG. 3A is a picture showing the blood sample in the device according to the embodiment of the invention before the electrodes are powered on;

FIG. 3B is a picture showing the blood sample in the device of FIG. 3A after the electrodes are powered on;

DETAILED DESCRIPTION OF THE INVENTION

The present invention will be apparent from the following detailed description, which proceeds with reference to the accompanying drawings, wherein the same references relate to the same elements.

In order to make the steps of the method for separating charged particles in a liquid sample more comprehensive, the structure and composition of the device for separating charged particles in a liquid sample will be illustrated in advance, and then the method applied to the device for testing the liquid sample of whole blood will be described. To be noted, the following embodiments and examples are only for illustrations and are not for limiting the present invention.

Figure 1:
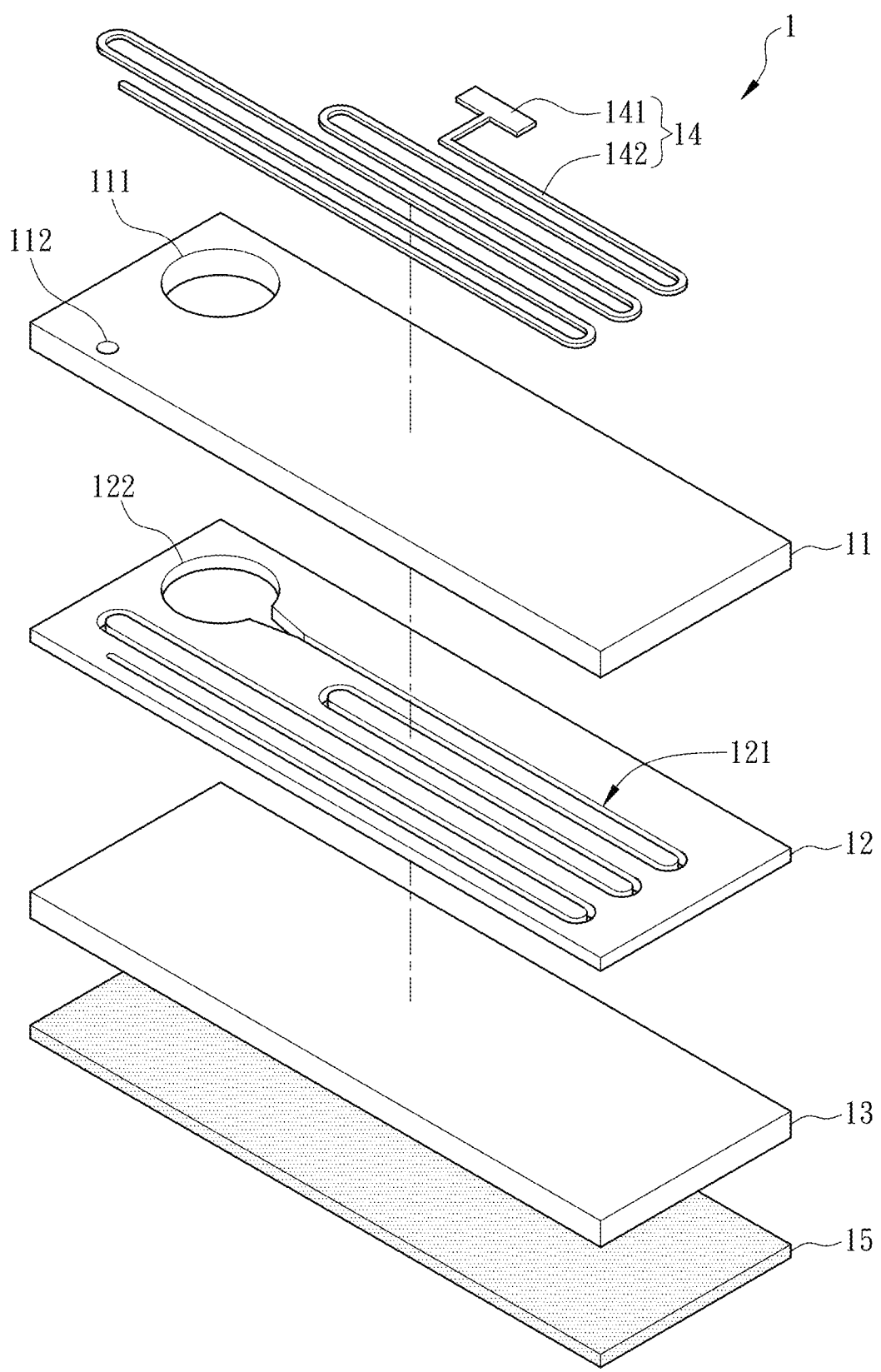
FIG. 1 is an exploded view of a device for separating charged particles in a liquid sample according to an embodiment of the invention.
Figure 2A:
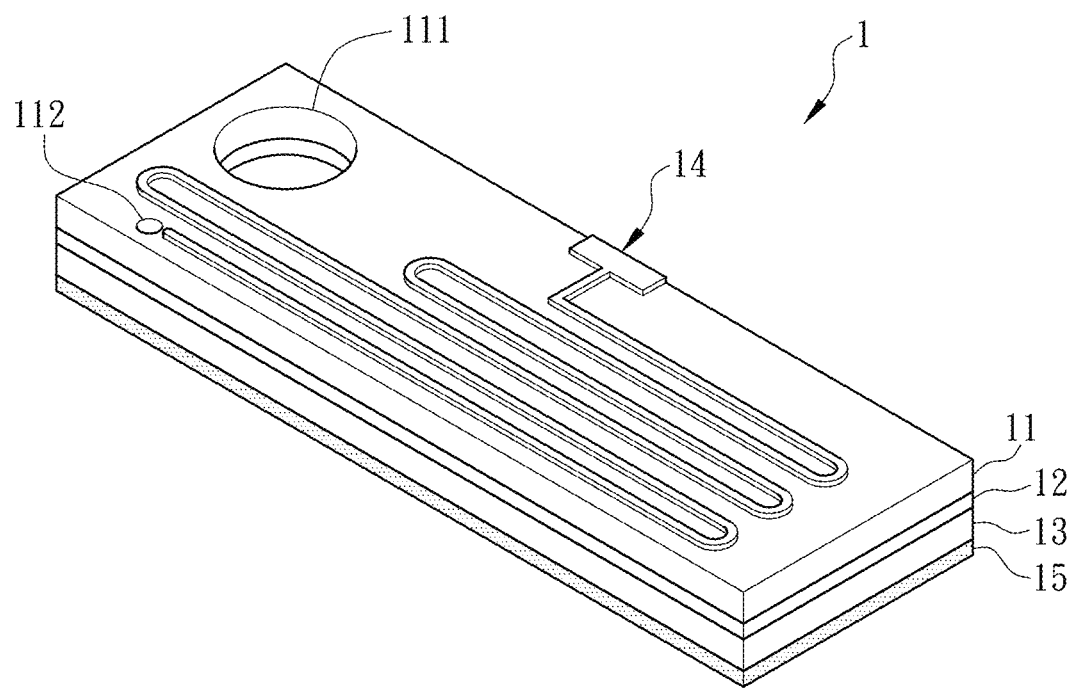
FIG. 2A is a schematic diagram showing the assembled device of FIG. 1.
Figure 2B:
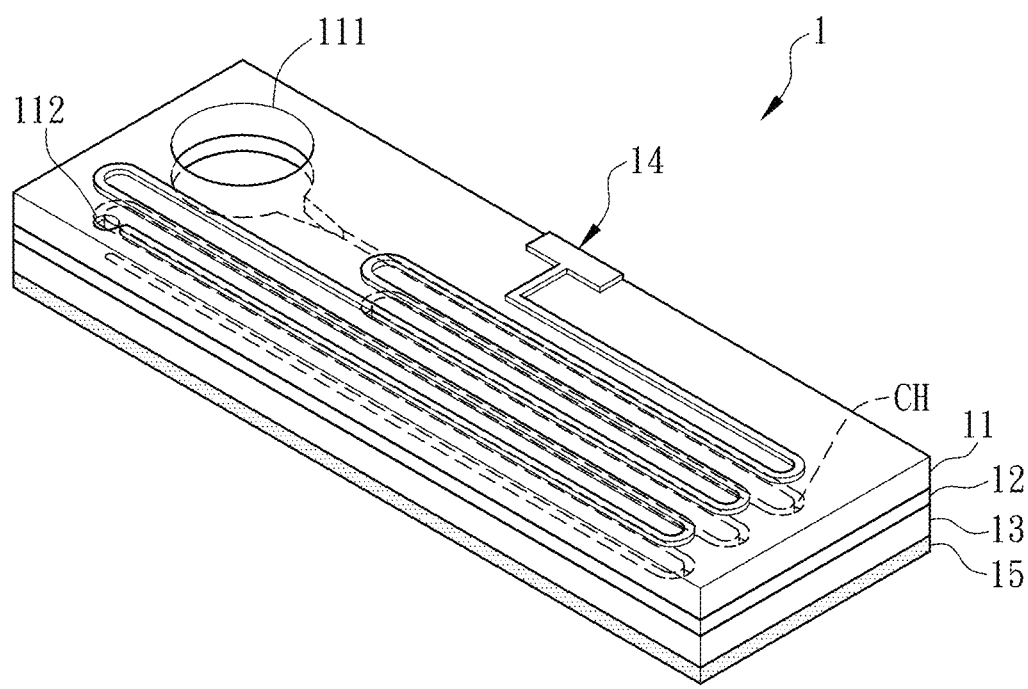
FIG. 2B is a perspective view of the assembled device of FIG. 1.

FIG. 1 is an exploded view of a device 1 for separating charged particles in a liquid sample according to an embodiment of the invention, FIG. 2A is a schematic diagram showing the assembled device 1 of FIG. 1, and FIG. 2B is a perspective view of the assembled device 1 of FIG. 1. In this embodiment, the device 1 includes an electrode 14, a cover layer 1.1, an interlaid layer 12, a substrate layer 13, and another electrode 15 in sequence. The substrate layer 13, the interlaid layer 12 and the cover layer 11 together define a channel CH. The above structure and relations are not for limitation. In other embodiments, the components of the device 1 may have different arrangements, or additional layers may be interposed between or around the above structure.

The cover layer 11 is configured with an opening 111 and an outlet 112, which are communicated with the channel CH, for inputting and outputting the blood sample or other liquid samples. The dimensions and shapes of the opening 111 and outlet 112 can be varied depending on the actual requires, and this invention is not limited. Preferably, the shapes of the opening 111 and outlet 112 are all circles, wherein the internal diameter of the opening 111 is about 11 mm, and the internal diameter of the outlet 112 is about 2 mm. The above structures on the cover layer 11 can be formed by the water-assisted laser processing.

In this embodiment, the material of the interlaid layer 12 comprises an optical paste or a photoresist material. Preferably, the interlaid layer 12 is made of, for example but not limited to, the optical clear adhesive (OCA) or JSR photoresist material. These preferred materials can further enhance the capillary attraction of the channel CH, thereby improving the transmission efficiency of the liquid sample. Accordingly, the device 1 does not need additional equipment for driving the liquid sample to flow. Besides, the photoresist material can provide thermal bonding at lower temperature, so that the process for fixing the interlaid layer 12 on a glass material (the cover layer 11 or the substrate layer 13) can be simplifier, and the process performance can be improved.

The interlaid layer 12 is partially configured with a through hole so as to form a continuous and wiggled channel structure 121. After combining the cover layer 11, the interlaid layer 12 and the substrate layer 13, two open sides of the channel structure 121 are mostly blocked so as to form the desired channel CH. Herein, only the specific positions of the channel CH are configured for inputting or outputting the liquid sample.

As shown in FIG. 1, the channel structure 121 has an injection hole 122 disposed corresponding to the opening 111. By combining the interlaid layer 12 and the substrate layer 13, the bottom of the injection hole 122 and the channel structure 121 are sealed, thereby forming a space for accommodating the blood inputted through the opening 111. This configuration can increase the sample amount in every injection for adjusting the inputted amount of the blood sample, and control the distance between two inputted liquid samples in the channel CH. Thus, the operation of the device 1 becomes more convenient The structure of the interlaid layer 12 can be formed by the following steps. Firstly, an optical paste or a photoresist material is attached on the top surface of the substrate layer 13. Next, the optical paste or photoresist material is treated by a water-assisted laser processing so as to form the channel structure 121 and the injection hole 122. Preferably, the interlaid layer 12 is made of the hydrophilic optical clear adhesive (OCA) or JSR photoresist material. Alternatively, the channel structure 121 and the injection hole 122 can be formed by, for example but not limited to, photolithography process or mechanical machining.

The electrodes 14 and 15 are correspondingly disposed on the cover layer 11 and the substrate layer 13, respectively. Referring to FIG. 1, the electrode 14 is disposed on the cover layer 11, and the electrode 15 is disposed underneath the substrate layer 13. The channel CH is located between the electrodes 14 and 15. In this embodiment, the shape and dimension of the electrode 14 are identical to the channel CH, and the shape and dimension of the electrode 15 are identical to the substrate layer 13. As shown in FIG. 1, the sides of the electrodes 14 and 15 opposite to each other have different surface areas and shapes so as to form a non-uniform electric field.

The electrodes 14 and 15 are configured opposite to each other but not in contact with each other, and they are not directly contact with the blood sample within the channel CH. This feature can prevent the denaturalization of the blood sample. In this embodiment, the electrode 14 has a contact portion 141 and a body portion 142. The contact portion 141 is connected with an external power source for providing the required power. The body portion 142 substantially cooperates with the other electrode 15 for generating a non-uniform electric field around the channel CH. The direction of the electric field is perpendicular o the flowing direction of the blood sample in the channel CH, so that the driving force of the electric filed and the momentum of the flowing blood sample are simultaneously applied to the charged blood cells in perpendicular directions. To be noted, the body portion 142 of the electrode 14 and the channel structure 121 (or the channel CH) have the same shape. Besides, the electrode 15 is a rectangular plate, and any point of the periphery of the rectangular plate can be used as a contact portion for connecting with an external power source.

The manufacturing method of the electrodes 14 and 15 are not limited to the above procedure. For example, the electrodes 14 and 15 can be made by disposing a thermal resist material or a photoresist material on the cover layer 11 and the substrate layer 13, defining the electrode patterns on the cover layer 11 and the substrate layer 13 by laser processing or photolithography process, and then coating a layer of electrode material thereon separately or simultaneously. Herein, the above photoresist material can be the same as or different from that used for forming the interlaid layer 12.

Referring to FIG. 2B, the electrode 14, the cover layer 11, the interlaid layer 12, the substrate layer 13 and the electrode 15 are stacked and fixed in sequence so as to form the device 1. Furthermore, the device 1 is a capacitive or resistive separating device. Besides, since the interlaid layer 12 is made of optical clear adhesive (OCA) or photoresist material, which has adhesive, it can provide thermal bonding at low temperature. The substrate layer 13, the cover layer 11 and the interlaid layer 12 can together define a continuous and wiggled channel CH as well as the opening 111 and the outlet 112, which are connected with two ends of the channel CH, respectively.

Figure 3A:
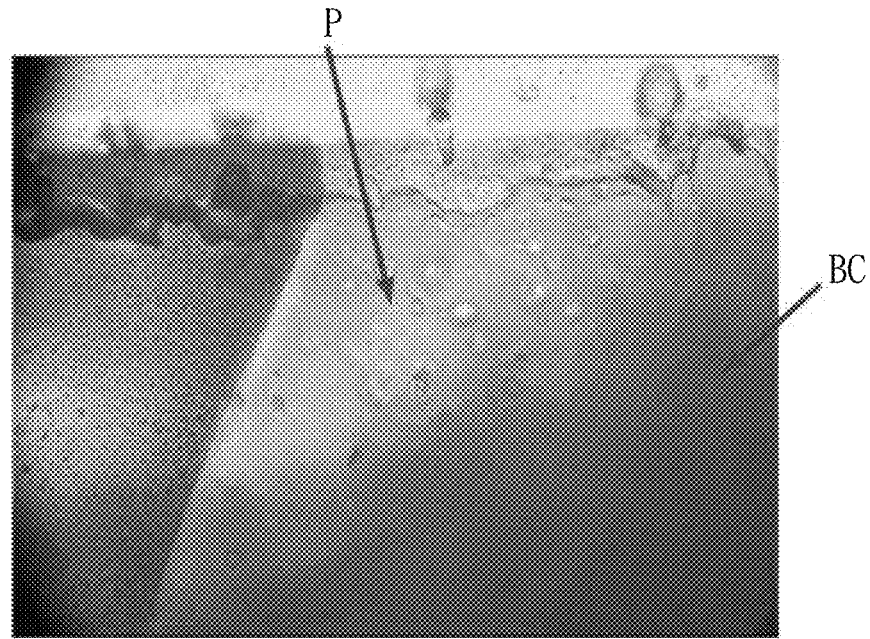
Figure 3B:
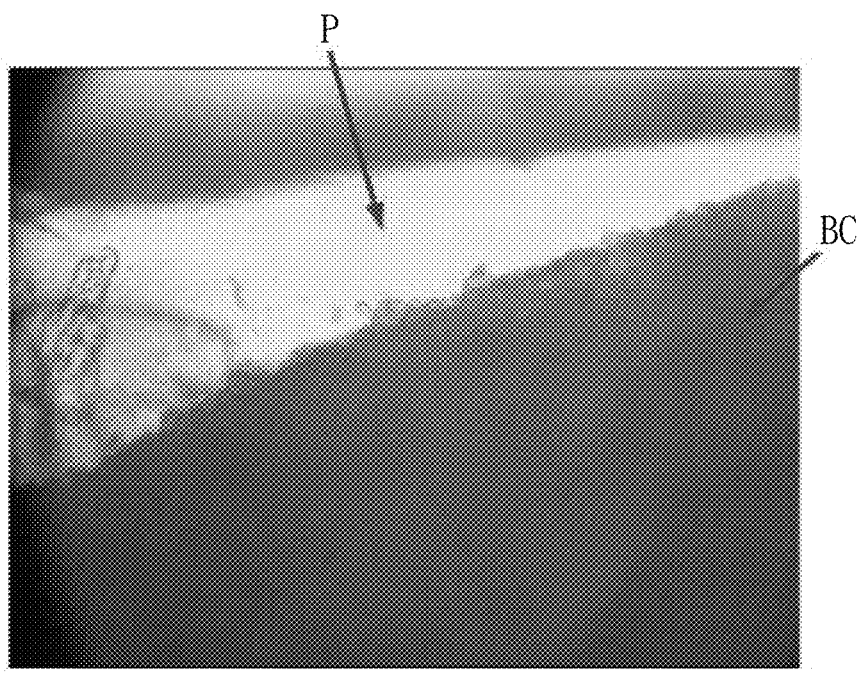

FIG. 3A is a picture showing the blood sample in the device according to the embodiment of the invention before the electrodes are powered on, and FIG. 3B is a picture showing the blood sample in the device of FIG. 3A after the electrodes are powered on. Referring to FIGS. 2B, 3A and 3B, before powered on, the blood cells BC and blood plasma P of the whole blood sample in the channel CH are well mixed without any separation phenomenon. After powered on through the electrodes 14 and 15, the electrodes 14 and 15 of different shapes and dimensions can provide a non-uniform electric field around the channel CH. When the whole blood sample flows through the non-uniform electric field, the charged blood cells BC are subjected to the electric field and then aggregated. Since the mass density of the blood cells BC (charged particles) is larger than the density of the blood plasma P (indicating the residual part of the liquid sample), the aggregated blood cells BC will have natural precipitation phenomenon due to the gravity. Moreover, the flow rate of the aggregated blood cells BC becomes slower or even to be stopped, so that the blood cells BC can be separated from the blood plasma P. Herein, the blood cells BC include red blood cells, white blood cells, and/or blood platelets.

Figure 4A:
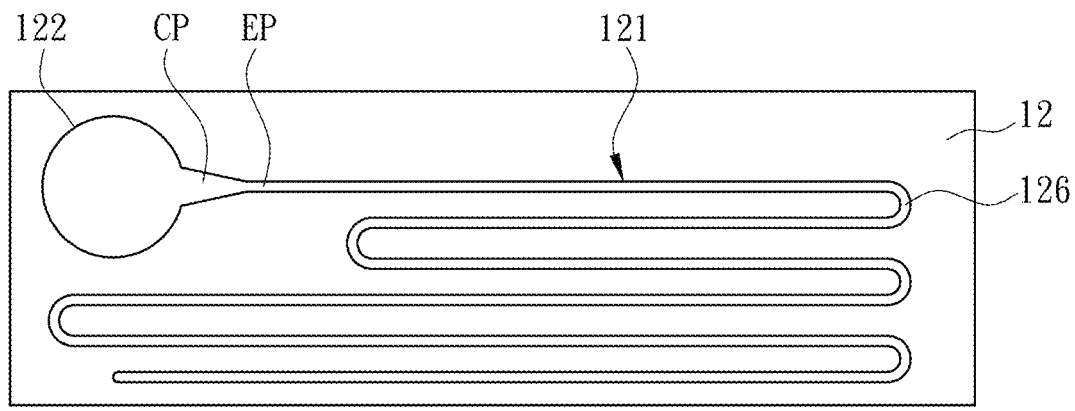
FIGS. 4A and 4B are top views showing the different interlaid layers of the device in FIG. 1.
Figure 4B:
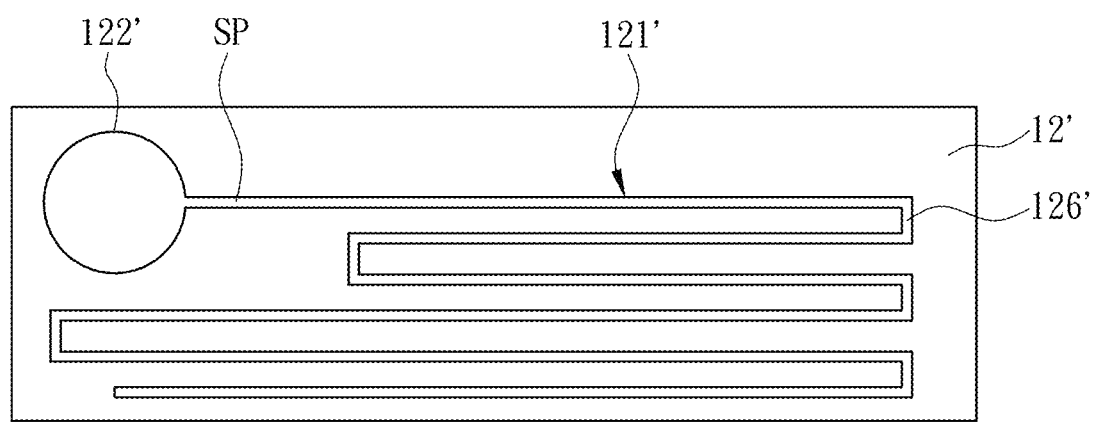

FIG. 4A is a top view of the interlaid layer of FIG. 1, and FIG. 4B is a top view showing a modified interlaid layer. Referring to FIGS. 1 and 4A, one end of the channel structure 121 close to the opening 111 has a larger internal diameter. In particular, the internal diameter of the channel structure 121 close to the injection hole 122 is gradually increased. Thus, the internal shape of the channel structure 121 forms a cone shape (the area CP), and an extension portion (area EP) is configured at one end of the cone shape. This configuration can prevent the overflow as injecting the blood sample, and enhance the capillary attraction for driving the blood sample to flow. Moreover, this cone-shaped structure can decrease the flowing resist so as to improve the flow of the blood sample. Besides, the channel structure 121 has at least a tuning portion 126 with a shape of arc, hairpin, hoof, or the likes, which can further decrease the flowing resist in the channel CH.

Of course, the channel structure of the invention may have many different aspects, which will be described hereinafter. Different from the above-mentioned interlaid layer 12, the interlaid layer 12' as shown in FIG. 4B has a channel structure 121' with a substantially uniform internal diameter (the area SP is a straight cylinder) at the injection hole 122'. Besides, the turning portion 126' of the channel structure 121' is a right angle. Compared with the cone-shaped structure of FIG. 4A, the flowing of the blood sample in the channel structure 121' of FIG. 4B is not smooth, but the manufacturing of the channel structure 121' is easier and cheaper.

In the above embodiments, the liquid sample is a blood sample or a whole blood sample. Of course, in other embodiments, the liquid sample can also be a fluid substance sample containing suspended matters, particles, or any other micro solid substances, which carry charges.

Figure 5:
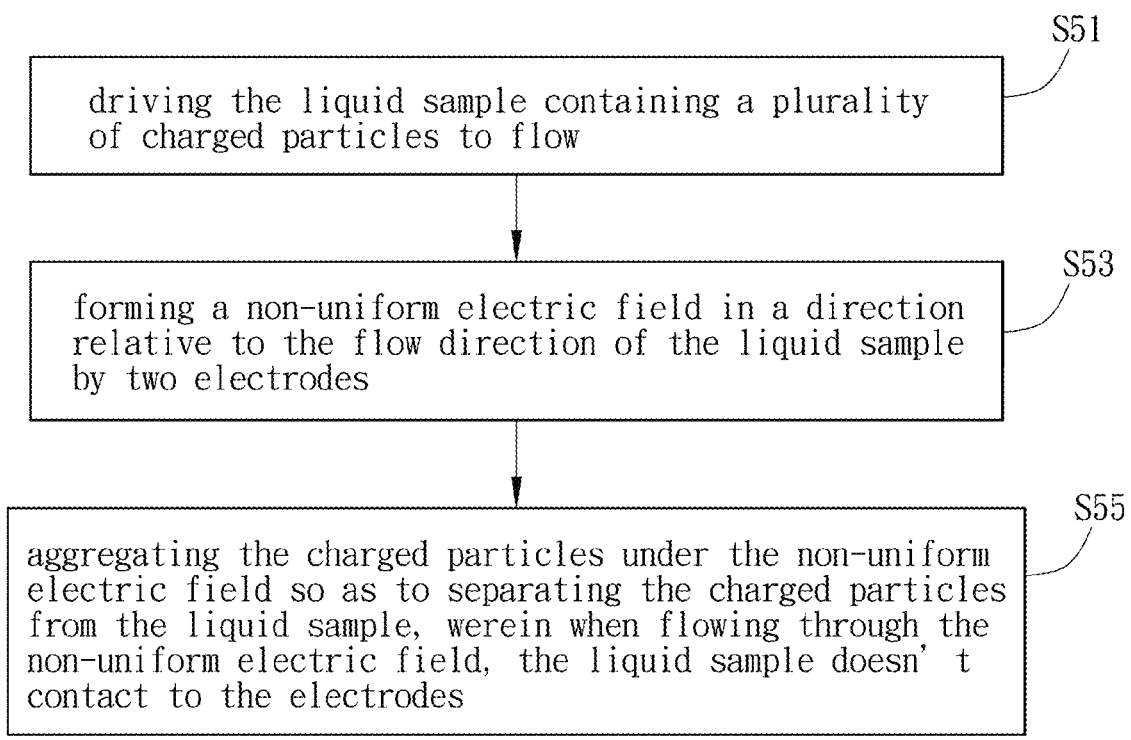
FIG. 5 is a flowchart of a method for separating charged particles in a liquid sample according to an embodiment of the invention.

FIG. 5 is a flowchart of a method for separating charged particles in a liquid sample according to an embodiment of the invention. Referring to FIG. 5, the method for separating charged particles in a liquid sample includes the following steps of: driving the liquid sample containing a plurality of charged particles to flow (step S51); forming a non-uniform electric field in a direction relative to the flow direction of the liquid sample by two electrodes (step S53); and aggregating the charged particles under the non-uniform electric field so as to separating the charged particles from the liquid sample (step S55). Herein, when flowing through the non-uniform electric field, the liquid sample doesn't contact to the electrodes. The components and device applied to this method as well as their operation theories and details have been described in the previous embodiments, so the detailed description thereof will be omitted. The following illustration is only to emphasize the concept of the method for separating charged particles in a liquid sample with reference to the flowchart of FIG. 5 and the device of FIG. 2A.

In practice, the liquid sample containing charged particles is injected through the opening 111, and then the liquid sample is driven by the capillary attraction and thus spontaneously flows in the channel CR When the charged particles flow in the channel CH and pass through the non-uniform electric field formed by the electrodes 14 and 15, the charged particles are affected by the electric field and aggregated. As the volume and weight of the aggregated charged particles increase, the gravity and/or resistance of the aggregated charged particles are also increased, thereby slowing down the aggregated charged particles. As a result, the aggregated charged particles can be separated from the liquid sample.

Figure 6:
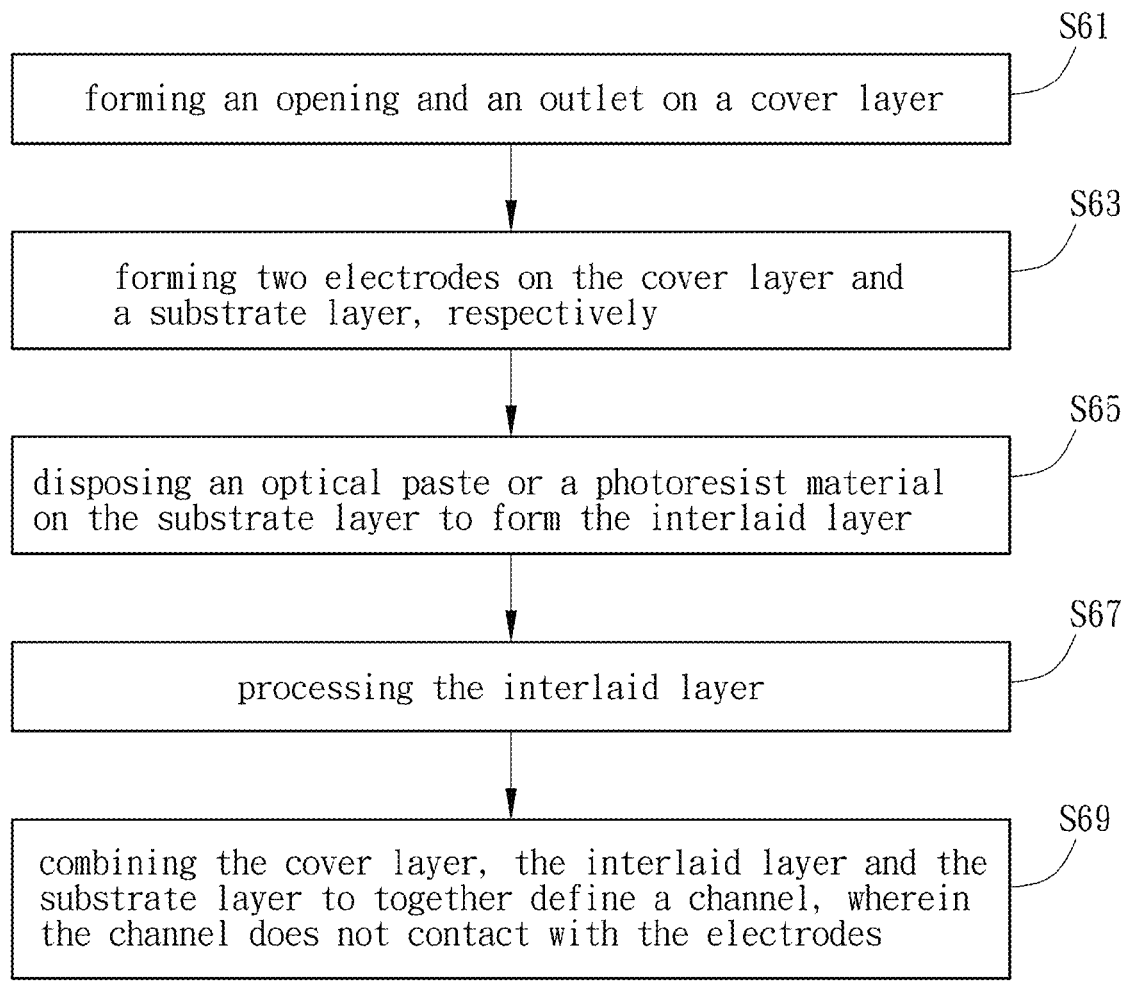
FIG. 6 is a flowchart of a manufacturing method of a device for separating charged particles in a liquid sample according to an embodiment of the invention.

FIG. 6 is a flowchart of a manufacturing method of a device for separating charged particles in a liquid sample according to an embodiment of the invention. Referring to FIG. 6, the manufacturing method of a device for separating charged particles in a liquid sample includes the following steps of: forming an opening and an outlet on a cover layer (step S61); forming two electrodes on the cover layer and a substrate layer, respectively (step S63); disposing an optical paste or a photoresist material on the substrate layer to form the interlaid layer (step S65); processing the interlaid layer (step S67); and combining the cover layer, the interlaid layer and the substrate layer to together define a channel, wherein the channel does not contact with the electrodes (step S69). The step of forming the electrodes (step S63) comprises to dispose a thermal resist material or another photoresist material on the cover layer and the substrate layer for defining the patterns of the electrodes and to coat a layer of electrode material thereon. Preferably, the patterns are defined by a laser machining or a photolithography process. The step of processing the interlaid layer (step S67) is to form a part of the channel by a laser machining, a photolithography process, or a mechanical machining. The cover layer, the interlaid layer and the substrate layer are combined by a low-temperature bonding process. The components of the device for separating charged particles in a liquid sample and their manufacturing method have been described in the above embodiments, so the detailed descriptions thereof will be omitted.

In summary, the method for separating charged particles in liquid sample is applied by making the liquid sample pass through a non-uniform electric field. The direction of the non-uniform electric field is relative to the flow direction of the sample; preferably, the direction of the non-uniform electric field is vertical to the flow direction of the sample. With the non-uniform electric field, the charged particles of the liquid sample are able to aggregate, further be separated from the liquid sample. With the above-mentioned techniques, users can collect separated charged particles or the liquid sample being separated.

With regard to the separating device, a substrate layer, an interlaid layer, a cover layer and two electrodes of the separating device defines a channel which is used for accommodating the liquid sample. The non-uniform electric field formed by the corresponding disposition of the two electrodes is applied to the liquid sample flowing through, further aggregating the charged particles and slowing down the flow rate. As mentioned above, the separating device of the present invention has simple structure. With some simple operating steps including insertion of the liquid sample and formation of the electric field, the separating device is advantageous for simple operation and quick separation.

Compared to the prior techniques, the method and device for separating charged particles in liquid sample and manufacturing method of the device of the present invention is suitable for separating whole blood and collecting blood plasma. The separation is done by aggregating the charged blood cells with non-uniform electric field, thus making the difference flow rate between the blood cells and blood plasma. The materials of the substrate layer and the upper layer are both hydrophilic, which driving the sample to be tested without external force and the need of pump, reducing the bulk and the manufacturing cost. In addition, the separating device is advantageous for its disposability, lower possibilities of the qualitative change and pollution of the sample. Moreover, the device is able to be applied without cleanness and special preprocessing.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A device for separating charged particles in a liquid sample, comprising:
    a substrate layer;
    an interlaid layer disposed on the substrate layer;
    a cover layer disposed on the interlaid layer, wherein the substrate layer, the interlaid layer and the cover layer together define a channel; and
    two electrodes correspondingly disposed on the cover layer and the substrate layer, respectively, wherein the electrodes do not contact with the liquid sample,
    wherein the sides of the electrodes opposite to each other have different surface areas so as to form a non-uniform electric field.

2. The device of claim 1, wherein the device is a capacitive or resistive separation chip, the liquid sample is a blood sample, and the charged particles are blood cells.

3. The device of claim 1, wherein the material of the substrate layer and the cover layer comprises glass, ITO, silicon oxide, or silicon.

4. The device of claim 1, wherein the material of the interlaid layer comprises an optical paste or a photoresist material.

5. The device of claim 1, wherein the cover layer has an opening and an outlet communicating with the channel, and an internal diameter of one end of the channel close to the opening is larger than that of another end of the channel.

6. The device of claim 1, wherein the channel has at least a turning portion with a shape of arc, hairpin, or hoof.

7. The device of claim 1, wherein one of the electrodes is disposed over the cover layer, and the other one thereof is disposed underneath the substrate layer.

8. The device of claim 1, wherein one of the electrodes has a shape and a dimension identical to the channel, and the other one thereof has a shape and a dimension identical to the substrate layer.

9. A method of manufacturing the device of claim 1, the manufacturing method comprising the steps of:
   forming an opening and an outlet on the cover layer;
   forming two electrodes on the cover layer and the substrate layer, respectively;
   disposing an optical paste or a photoresist material on the substrate layer to form the interlaid layer;
   processing the interlaid layer; and
   combining the cover layer, the interlaid layer and the substrate layer to together define a channel, wherein the channel does not contact with the electrodes.

10. The manufacturing method of claim 9, wherein the step of forming the electrodes comprises to dispose a thermal resist material or another photoresist material on the cover layer and the substrate layer for defining the patterns of the electrodes and to coat a layer of electrode material thereon.

11. The manufacturing method of claim 10, wherein the patterns are defined by a laser machining or a photolithography process.

12. The manufacturing method of claim 9, wherein the step of processing the interlaid layer is to form a part of the channel by a laser machining, a photolithography process, or a mechanical machining.

13. The manufacturing method of claim 9, wherein the cover layer, the interlaid layer and the substrate layer are combined by a low-temperature bonding process.

14. A manufacturing method of a device for separating charged particles in a liquid sample, wherein the device comprises a substrate layer, an interlaid layer, a cover layer and two electrodes, the manufacturing method comprising the steps of:
   forming an opening and an outlet on the cover layer;
   forming two electrodes on the cover layer and the substrate layer, respectively;
   disposing an optical paste or a photoresist material on the substrate layer to form the interlaid layer;
   processing the interlaid layer; and
   combining the cover layer, the interlaid layer and the substrate layer to together define a channel, wherein the channel does not contact with the electrodes;
   wherein, the interlaid layer is disposed on the substrate layer, the cover layer is disposed on the interlaid layer, the electrodes do not contact with the liquid sample, and the sides of the electrodes opposite to each other have different surface areas so as to form a non-uniform electric field.

15. The manufacturing method of claim 14, wherein the step of forming the electrodes comprises to dispose a thermal resist material or another photoresist material on the cover layer and the substrate layer for defining the patterns of the electrodes and to coat a layer of electrode material thereon.

16. The manufacturing method of claim 14, wherein the patterns are defined by a laser machining or a photolithography process.

17. The manufacturing method of claim 14, wherein the cover layer, the interlaid layer and the substrate layer are combined by a low-temperature bonding process.

* * * * *